(12) United States Patent
Hatagishi et al.

(10) Patent No.: US 9,052,139 B2
(45) Date of Patent: Jun. 9, 2015

(54) CATALYST AND PROCESS FOR PRODUCING THE SAME

(75) Inventors: Takuya Hatagishi, Numazu (JP); Tomohiro Yamada, Numazu (JP)

(73) Assignee: MEIDENSHA CORPORATION, Tokyo (JP)

(*) Notice: Subject to any disclaimer, the term of this patent is extended or adjusted under 35 U.S.C. 154(b) by 427 days.

(21) Appl. No.: 12/988,072

(22) PCT Filed: Apr. 13, 2009

(86) PCT No.: PCT/JP2009/057451
§ 371 (c)(1),
(2), (4) Date: Oct. 15, 2010

(87) PCT Pub. No.: WO2009/128426
PCT Pub. Date: Oct. 22, 2009

(65) Prior Publication Data
US 2011/0034321 A1 Feb. 10, 2011

(30) Foreign Application Priority Data

Apr. 18, 2008 (JP) .................................. 2008-108713
Feb. 20, 2009 (JP) .................................. 2009-038276

(51) Int. Cl.
| | |
|---|---|
| *B01J 29/06* | (2006.01) |
| *B01J 29/44* | (2006.01) |
| *B01J 29/16* | (2006.01) |
| *B01J 29/12* | (2006.01) |
| *B01J 29/48* | (2006.01) |
| *F26B 3/12* | (2006.01) |
| *B01J 29/076* | (2006.01) |
| *B01J 29/40* | (2006.01) |
| *B01J 35/00* | (2006.01) |
| *B01J 35/02* | (2006.01) |
| *B01J 37/00* | (2006.01) |
| *C07C 2/76* | (2006.01) |
| *B01J 29/08* | (2006.01) |
| *B01J 29/70* | (2006.01) |
| *B01J 29/78* | (2006.01) |

(52) U.S. Cl.
CPC . *F26B 3/12* (2013.01); *B01J 29/06* (2013.01);
*B01J 29/076* (2013.01); *B01J 29/08* (2013.01);
*B01J 29/16* (2013.01); *B01J 29/40* (2013.01);
*B01J 29/48* (2013.01); *B01J 29/70* (2013.01);
*B01J 29/78* (2013.01); *B01J 35/002* (2013.01);
*B01J 35/023* (2013.01); *B01J 37/0036*
(2013.01); *B01J 37/0045* (2013.01); *B01J
2229/186* (2013.01); *C07C 2/76* (2013.01);
*C07C 2521/06* (2013.01); *C07C 2521/08*
(2013.01); *C07C 2521/12* (2013.01); *C07C
2523/22* (2013.01); *C07C 2523/26* (2013.01);
*C07C 2523/28* (2013.01); *C07C 2523/30*
(2013.01); *C07C 2523/36* (2013.01); *C07C
2529/06* (2013.01); *C07C 2529/08* (2013.01);
*C07C 2529/40* (2013.01); *C07C 2529/83*
(2013.01); *C07C 2529/89* (2013.01)

(58) Field of Classification Search
USPC .................................... 502/60, 73, 77, 85, 87
See application file for complete search history.

(56) References Cited

U.S. PATENT DOCUMENTS

| | | | | |
|---|---|---|---|---|
| 4,196,102 A | * | 4/1980 | Inooka et al. | 502/62 |
| 4,975,180 A | * | 12/1990 | Eberly | 208/114 |
| 5,011,667 A | * | 4/1991 | Kuznicki et al. | 423/716 |
| 5,369,071 A | * | 11/1994 | Degnan et al. | 502/71 |
| 5,552,361 A | * | 9/1996 | Rieser et al. | 502/208 |
| 5,569,634 A | * | 10/1996 | Miller et al. | 502/64 |
| 6,211,104 B1 | * | 4/2001 | Shi et al. | 502/67 |
| 6,552,243 B2 | | 4/2003 | Allison et al. | |
| 6,864,202 B2 | * | 3/2005 | Sarkar et al. | 502/65 |
| 7,179,766 B2 | | 2/2007 | Wolfe et al. | |
| 7,557,256 B2 | | 7/2009 | Chang et al. | |
| 2002/0049133 A1 | * | 4/2002 | Ziebarth et al. | 502/64 |
| 2003/0018228 A1 | * | 1/2003 | Vaughn et al. | 585/500 |
| 2004/0092386 A1 | * | 5/2004 | Brady et al. | 502/64 |
| 2005/0020867 A1 | * | 1/2005 | Xie et al. | 585/651 |
| 2005/0146066 A1 | * | 7/2005 | Koide et al. | 264/44 |

(Continued)

FOREIGN PATENT DOCUMENTS

| | | |
|---|---|---|
| JP | 61-266306 A | 11/1986 |
| JP | 1-236947 A | 9/1989 |
| JP | 10-272366 A | 10/1998 |
| JP | 11-060514 A | 3/1999 |
| JP | 2003-026613 A | 1/2003 |
| JP | 2004-521070 A | 7/2004 |
| JP | 2005-255605 A | 9/2005 |

(Continued)

OTHER PUBLICATIONS

F. Solymosi et al., "Aromatization of Methane over Supported and Unsupported Mo-Based Catalysts", *Journal of Catalysis*, vol. 165, (1997), pp. 150-161.

*Primary Examiner* — Elizabeth Wood
(74) *Attorney, Agent, or Firm* — Foley & Lardner LLP

(57) ABSTRACT

[Task] To provide a catalyst in which granules of the catalyst are improved in crash strength with no use of the caking agent, while increasing the effective area of the crystal surface part of the catalyst.

[Solving Means] A catalyst powder-containing slurry obtained by milling a metallosilicate-containing raw material by a bead mill is dried by a spray drying method to obtain granules of a catalyst. The raw material may be one containing a metallosilicate having micropores of a size that is substantially 4.5 to 6.5 angstroms. It is better to mill the raw material by a bead mill such that the particle size of the metallosilicate becomes 1.0 μm or less at a cumulative frequency of 50%. It is better that as a metal component at least one metal component selected from rhenium, vanadium, molybdenum, tungsten, chromium, and their compounds is supported on the metallosilicate. It is better to subject the slurry to the drying process after aging. It is better to add polyvinyl alcohol to the slurry.

8 Claims, 6 Drawing Sheets

(56) References Cited

U.S. PATENT DOCUMENTS

| | | | |
|---|---|---|---|
| 2006/0183626 A1* | 8/2006 | Cavalcanti et al. | 502/5 |
| 2007/0219082 A1* | 9/2007 | Goto et al. | 502/60 |
| 2007/0260100 A1* | 11/2007 | Cheng et al. | 585/640 |
| 2007/0293709 A1* | 12/2007 | Iaccino et al. | 585/312 |
| 2009/0288985 A1 | 11/2009 | Long et al. | |

FOREIGN PATENT DOCUMENTS

| | | | |
|---|---|---|---|
| JP | 2005-305221 A | | 11/2005 |
| JP | 2007-075796 A | | 3/2007 |
| JP | 2007-527937 A | | 10/2007 |
| WO | WO 00/37176 | * | 6/2000 |
| WO | WO 2005/028105 A1 | | 3/2005 |

* cited by examiner

ELECTRON MICROSCOPE IMAGE 1 | O Kα1 | Al Kα1
Si Kα1 | Mo Lα1

ELECTRON MICROSCOPE IMAGE 1 | O Kα1 | Al Kα1
Si Kα1 | Mo Lα1

CATALYST AND PROCESS FOR PRODUCING THE SAME

TECHNICAL FIELD

This invention relates to a high-degree use of natural gas, biogas and methane hydrate, in which methane is a main component. Natural gas, biogas and methane hydrate are regarded as the most effective energy resources as a measure to counter global warming, and therefore an interest in techniques using them has grown. Methane resource attracts attention as a novel organic resource in the next generation or as a hydrogen resource for use in fuel cells, by making use of its clean characteristic. The present invention relates to a catalytic, chemical conversion technique and a catalyst production method, for efficiently producing aromatic compounds, in which benzene and naphthalene are main components, which are raw materials of chemical products, such as plastics, and a high purity hydrogen gas, from methane.

BACKGROUND TECHNIQUE

As a process for producing aromatic compounds, such as benzene, and hydrogen from methane, one is known in which methane is reacted in the presence of a catalyst. As the catalyst on this occasion, molybdenum supported on a ZSM-5 series zeolite is said to be effective (Non-patent Publication 1, Patent Publication 1, and Patent Publication 2). Even in the case of using these catalysts, however, there occur problems that carbon is precipitated in a large amount, and the carbon precipitation causes the catalyst activity to deteriorate in a short time and causes conversion of methane to be low.

In order to improve this problem, there has been a study in which the catalyst is shaped into pellet type, which is usable in a fixed bed type reaction facility, and the proportion of the catalyst component contained in the pellets is increased to achieve an efficient reaction with methane. In the case of the fixed bed reaction type, however, there has been a problem, since it becomes essential to use at least 10% of inorganic and organic caking agents in terms of mechanical strength, and since the size is limited to millimeter unit or more.

As shown in Patent Publication 3, there is also a study on the catalyst having a grain shape that is usable in a flow bed type reaction facility. However, the proportion of the catalyst component existing in the grains becomes 50% or lower from the viewpoints of wear resistance and impact resistance. This is inferior to the pellet type of a fixed bed type of the mechanical strength adjustment. Furthermore, since the catalyst is deactivated in a short period of time, it is essential to regenerate the catalyst.

PRIOR ART PUBLICATIONS

Non-Patent Publication

Non-patent Publication 1: JOURNAL OF CATALYSIS, 1997, pp. 165, vol. 150-161

Patent Publications

Patent Publication 1: Japanese Patent Application Publication Heisei 10-272366
Patent Publication 2: Japanese Patent Application Publication Heisei 11-60514
Patent Publication 3: Japanese Patent Application Publication Showa 61-266306

SUMMARY OF THE INVENTION

Task to be Solved by the Invention

In order to improve conversion of methane, it is essential to improve the efficiency of the contact between the reaction gas and the catalyst. The catalyst shape also gives a large influence to the reaction process. The shape is roughly classified into a pellet-type shaped body for fixed bed and granules for flow bed and moving bed. In the pellet-type shaped body, it is necessary to have materials other than the catalyst, which are necessary upon shaping, such as organic caking additive, inorganic caking additive, glass fibers, and pore-forming material. Thus, it is also necessary to consider the influence of these additives on the catalyst.

In the case of granules, there is an advantage that the efficiency of contact with the reaction gas is improved due to their small particle size of several tens of micrometers to several hundreds of micrometers. On the other hand, it is necessary to make the granules themselves flow in the reaction process. Therefore, it is essential that the granules are superior in wear resistance and thermal impact resistance. To satisfy these, it is necessary to mix or coat the granules with a large amount of the caking additive, besides the catalyst material. In particular, according to Patent Publication 3, it is possible to obtain roughly spherical granules of the catalyst by spray drying only a raw material zeolite powder slurry, but they are easily broken by the action of transportation or the like and vibration. Therefore, it is necessary to mix a suitable caking agent, besides the raw material zeolite powder.

Means For Solving The Task

Thus, a catalyst production process for solving the task is a catalyst production process for producing aromatic compounds and hydrogen from a lower hydrocarbon. It obtains granules of the catalyst by drying by a spray drying method a slurry containing a catalyst powder obtained by milling a metallosilicate-containing raw material.

Furthermore, the catalyst for solving the task is a catalyst prepared by the production process.

The metallosilicate-containing raw material may be one containing a metallosilicate having micropores of a size that is substantially 4.5 to 6.5 angstroms. It is better to mill the metallosilicate raw material by a bead mill such that the particle size of the metallosilicate becomes 1.0 µm or less at a cumulative frequency of 50%. It is better that at least one metal component selected from rhenium, vanadium, molybdenum, tungsten, chromium, and their compounds is supported on the metallosilicate. It is better that the amount of the molybdenum supported is 2-12 weight % relative to the total amount of the catalyst powder. It is better to dry the slurry by the spray drying method after aging. As the aging, it is possible to mention standing still under an atmosphere of an air of normal temperature and normal pressure. It is better that the metal component is supported on the metallosilicate by adding the metal component to the slurry. Furthermore, it is optional to add polyvinyl alcohol (hereinafter referred to as PVA) to the slurry.

Advantageous Effect Of The Invention

According to the above-mentioned catalyst production process of the invention, it is possible to provide a catalyst in which granules of the catalyst are improved in crash strength with no use of the caking agent, while increasing the effective area of the crystalline surface part of the catalyst.

MODE FOR CARRYING OUT THE INVENTION

Figure 1:
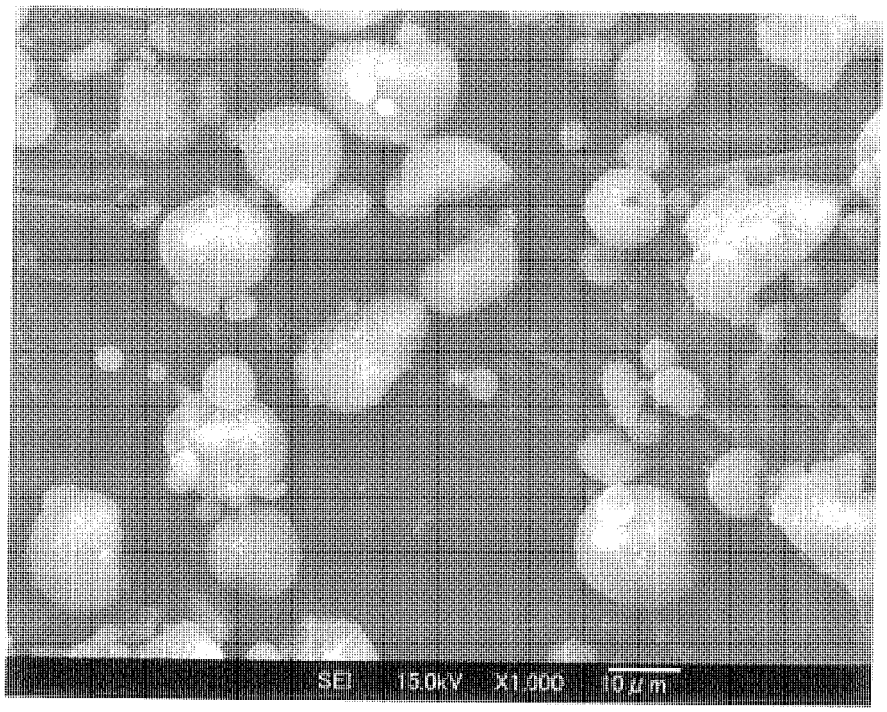
FIG. 1 is an SEM photograph (accelerating voltage: 15.0 kV; magnification: 1,000) of granules of Example 1.

In a catalyst-containing slurry in which a metallosilicate-containing raw material has been milled and highly dispersed by a bead mill, it is converted to granules by spray drying immediately after the slurry preparation or after conducting aging for a given period of time in the catalyst production process according to the present invention. It is possible to conduct the aging by allowing the slurry to stand still under an atmosphere of an air of normal temperature and normal pressure.

(1) Catalyst Support

The metallosilicate-containing raw material contains as a catalyst material at least one metal component selected from rhenium, vanadium, molybdenum, tungsten, chromium, and their compounds and contains as a support, which supports this catalyst material, a metallosilicate having micropores of a size that is substantially 4.5 to 6.5 angstroms. The metallosilicate is illustrated in Japanese Patent Application Publication 2004-97891. Specifically, as the metallosilicate (a porous metallosilicate), for example, in the case of aluminosilicate, it is possible to mention molecular sieve 5A, faujasite (NaY and NaX), ZSM-5, and MCM-22, which are porous bodies formed of silica and alumina. Furthermore, it can be exemplified by a zeolite support, which is a porous body, in which phosphoric acid is a major component, and which is characterized by comprising micropores or channels of 6-13 angstroms, such as ALPO-5 and VPI-5, and a mesomicroporous support, which contains silica as a major component and partially contains alumina as a component, and which is characterized by cylindrical micropores (channels) of mesomicropores (10-1,000 angstroms), such as FSM-16 and MCM-41. Furthermore, besides the aluminasilicate, a metallosilicate formed of silica and titania, etc. can also be used as the catalyst.

(2) Supporting of Supported Metal on Catalyst Support

It is a preferable method in which molybdenum of a predetermined concentration is supported by impregnation on a metallosilicate as a support. The amount of molybdenum supported is preferably 2-12 wt % relative to the total amount of the catalyst after baking.

It is better to add PVA to the slurry. In the case of baking granules obtained by drying by the spray drying method the slurry containing the catalyst powder milled by a bead mill, gas is generated in the granules during the baking. With this, the spherical granules burst, and there occurs a phenomena to generate defects in the spherical granules. If PVA is added, PVA is vaporized and removed during the baking to produce many micropores in the granules. The gas escapes from this gas pore to the outside. With this, it is possible to prevent the burst and generation of the defects. The amount of PVA to be added is preferably 0.1-1 wt % relative to the metallosilicate in the slurry.

(3) Milling of Catalyst Powder

There is mentioned a process for preparing a slurry obtained by milling by a bead mill a metallosilicate raw material or a metallosilicate, which supports the metal component, into 1 micrometer or less. The metallosilicate raw material or the metallosilicate supporting the metal component (hereinafter, catalyst powder) is weighed relative to water to make a slurry solution, for example, to have a ratio of catalyst powder: water=1:4. The mixing ratio is not limited to this, and it is preferable to make a suitable adjustment depending on the properties of the metallosilicate used. The slurry viscosity on that occasion is preferably 100 cps or lower. Upon mixing the catalyst powder and water, the total amount of water is previously put into a mixer, and then the catalyst powder is added under stirring by adjusting at about 0.4-1 kg per minute. If it is faster than this, the catalyst powder coagulates and precipitates in the mixer. Therefore, it is not preferable. On this occasion, there is used one that can arbitrarily set the blade shape and the speed of rotation. In particular, the blade shape and the speed of rotation are not limited.

Zirconia is preferable for the milling beads used in the bead mill.

By using the bead mill of the above specification, a hose pump for circulating the slurry is energized to conduct milling of the catalyst powder. The milling can be adjusted together with the bead size and the time. It is better to mill the metallosilicate raw material by the bead mill such that the particle size of the metallosilicate becomes 1.0 μm or less at a cumulative frequency of 50%. For example, in the case of ZSM-5 raw material of an average particle size of 42 μm, a milling to 0.3 μm becomes possible by a milling time of 1 hour. The slurry obtained by milling the catalyst powder is recovered by switching the supply line from closed system to open system.

(4) Granulation

A method for drying and granulating the catalyst powder in the slurry with a spray dryer is mentioned. It is preferable to directly dry and granulate the slurry prepared by (3) with a spray dryer or use it after aging for a given time (e.g., 6 days). Although the type of the spray dryer is not particularly limited, a downward spray, parallel flow system is preferable. The nozzle is preferably of a two-liquid nozzle system. It is preferable to suitably change the orifice diameter, depending on the slurry viscosity and the particle shape of the catalyst powder. Operation condition of the spray dryer is suitably adjusted depending on the slurry viscosity and the particle size of the catalyst powder in the slurry. The operation condition is not particularly limited.

According to the catalyst production process of the present invention, it is possible to provide a catalyst that has an increased effective area of the catalyst crystal surface part by milling of the catalyst powder of nanometer size and that has an improved crash strength of the catalyst granules even if no caking agent is added. Therefore, it becomes easily possible to produce spherical granules, which has been difficult in rolling granulation method. Furthermore, it becomes possible to omit or greatly reduce the inorganic caking agent. With this, it becomes easy to support the metal on the catalyst powder contained in the granules.

Furthermore, it becomes easy to uniformly support the metal on the catalyst powder and is possible to provide a catalyst that is superior in flow property of the granules and is improved in crash strength, by impregnating the catalyst powder with the metal component by adding the metal component to the milled catalyst powder-containing slurry. Crash strength of the granules becomes further higher by adding PVA to the slurry.

In the following, examples according to the invention and comparative example are shown.

COMPARATIVE EXAMPLE 1

As a catalyst powder according to Comparative Example 1, there was used a type of metallosilicate, a proton-type ZSM-5, having an average particle size of 31 μm and a crystalline size of 0.08 μm. The particle size and crystalline size were measured by calculating the average values of the particles selected at random from an electron microscope photograph. A slurry was prepared to have a solid matter concentration of 20wt % by using purified water as solvent.

This slurry was stirred for 1 hr and then granulated by a spray dryer (Type DL-41 made by YAMATO SCIENTIFIC CO., LTD.). After setting the operation conditions to have an inlet temperature of 230-240° C. and an outlet temperature of 90° C., drying and granulation were conducted with a dry air rate of 0.8 m$^3$/min, a nozzle spray air pressure of 0.1 MPa, and a slurry feed rate of 20 g/min. The obtained granules were dried in the air at 120° C. for 20 hr. Regarding strength of the granules, crash strength of each particle was measured in accordance with JIS Z8841. Crash strength of 15 granules obtained was measured. As shown in Table 3, every granule was less than 0.06 gf/mm$^2$, which was the measurement limit value of the measuring apparatus.

EXAMPLE 1

As a catalyst powder according to Example 1, there was used a type of metallosilicate, ZSM-5, having an average particle size of 42 μm and a crystalline size of 5 μm. The catalyst powder raw material was of ammonia-type and converted to proton-type by conducting a baking treatment at a predetermined temperature. Metal was not supported on ZSM-5 used in the present example.

Firstly, the milling method of the catalyst powder by a bead mill is described. 4 kg of purified water was weighed relative to 1 kg of the catalyst powder, and the total amount of the purified water was put into a stirring container. While rotating a blade of a stirrer, the total amount of the catalyst powder was added at 400 g/minute. After that, a slurry-circulating pump was energized, and it was started to circulate and mill the slurry. A part of the slurry was taken out at an interval of 15 minutes after the start to measure the slurry viscosity and the particle size distribution of the catalyst powder. Table 1 shows the change with time of the particle size distribution of the catalyst powder. 1 hr after the start of the milling, the circulating pump was stopped, and the slurry in the system was taken. The recovered slurry was 3.76 kg relative to 5 kg of the added slurry weight.

Then, the granulation method of the catalyst powder by a spray dryer is explained. The slurry formerly prepared was subjected to an aging for 5 days. In the aging, the slurry was allowed to stand still in the atmosphere of air of normal temperature and normal pressure. Then, the stirring was conducted in a stirring container. After setting at an inlet temperature of 230-240° C. and an outlet temperature of 90° C., drying and granulation were started by a spray dryer (Type DL-41 made by YAMATO SCIENTIFIC CO., LTD.) under conditions of a dry air wind rate of 0.8 m$^3$/min, a nozzle spray air pressure of 0.1 MPa, and a slurry feed rate of 20 g/min. The obtained granules were dried in the air at 120° C. for 20 hr. The SEM (scanning electron microscope) photograph after the drying is shown in FIG. 1. The result (the average value of 10 points) of crash strength of the granules is shown in Table 3.

EXAMPLE 2

Figure 2:
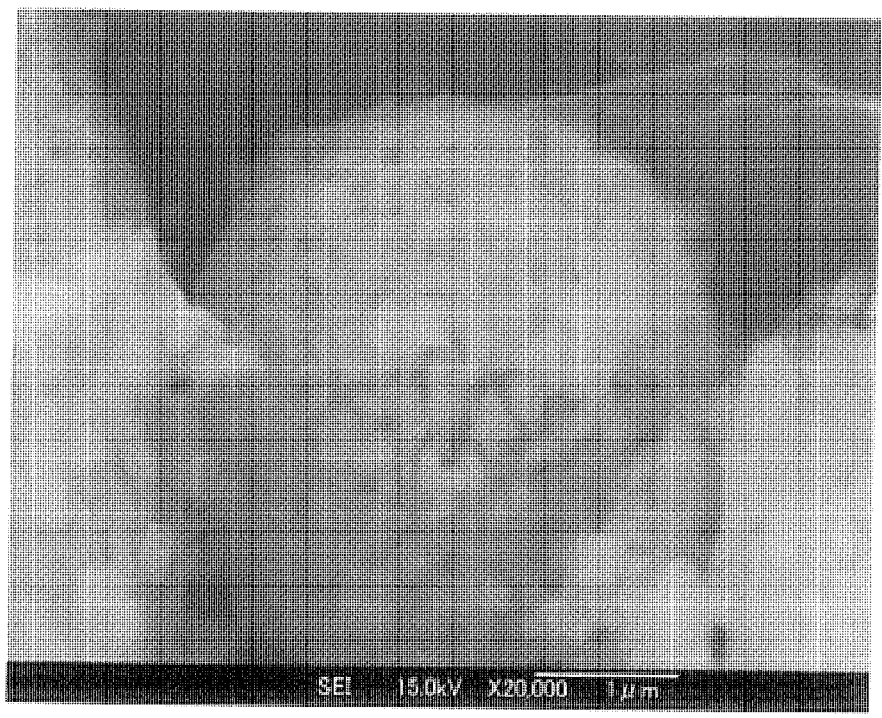
FIG. 2 is an SEM photograph (accelerating voltage: 15.0 kV; magnification: 20,000) of granules of Example 1.
Figure 3:
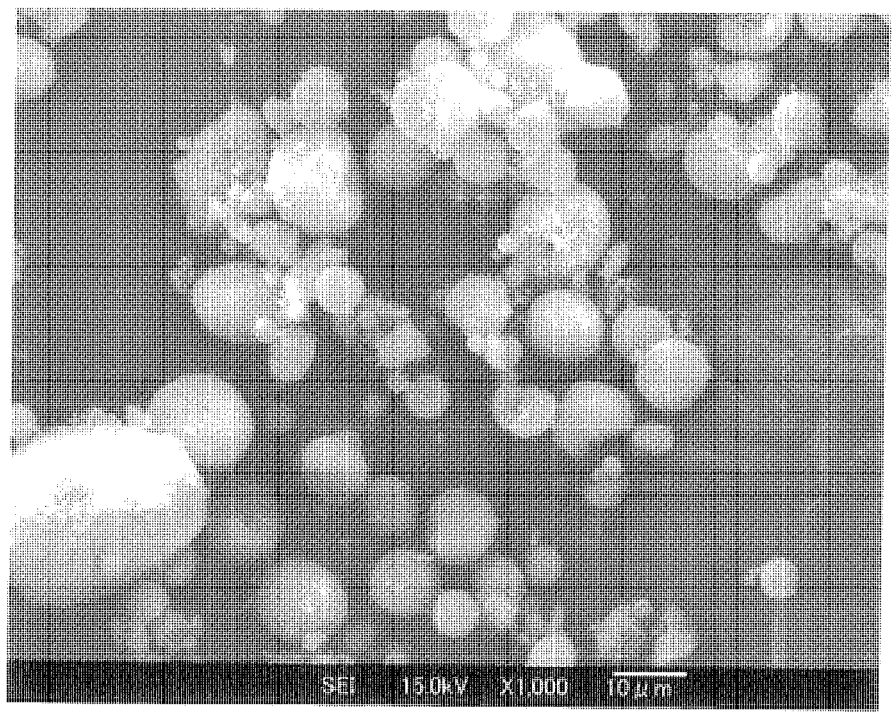
FIG. 3 is an SEM photograph (accelerating voltage: 15.0 kV; magnification: 1,000) of granules of Example 2.
Figure 4:
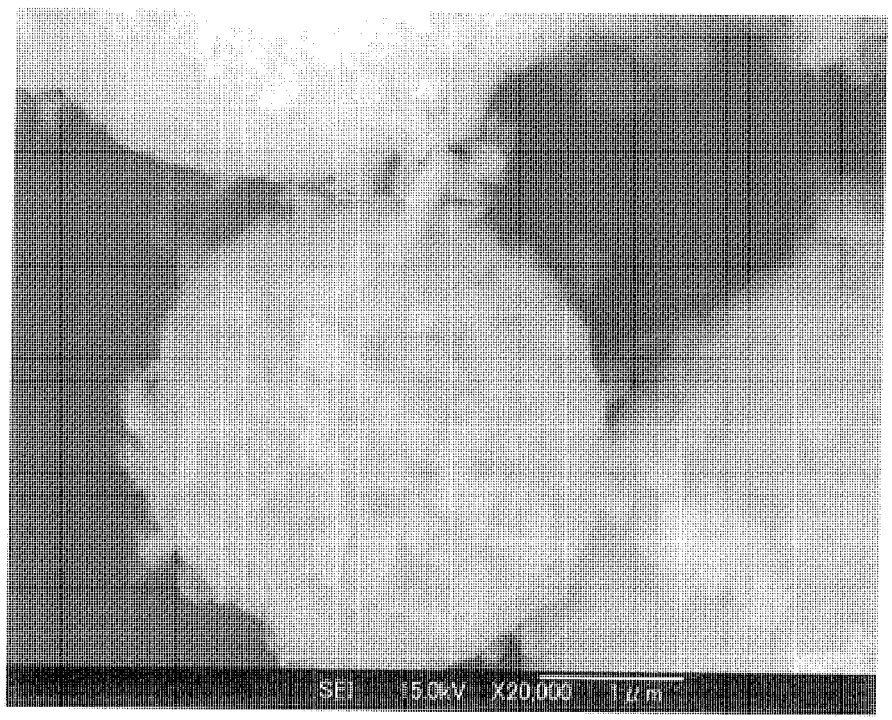
FIG. 4 is an SEM photograph (accelerating voltage: 15.0 kV; magnification: 20,000) of granules of Example 2.

As a catalyst powder according to Example 2, there was used a type of metallosilicate, ZSM-5, having an average particle size of 39 μm and a crystalline size of 4.2 μm. The subsequent preparation conditions are similar to Example 1. Table 2 shows the change of the particle size distribution of the catalyst powder milled by the bead mill. The SEM photograph of the granules by the spray dryer (Type DL-41 made by YAMATO SCIENTIFIC CO., LTD.) is shown in FIG. 2. Although not shown in Table 3, it was confirmed that crash strength of the granules according to Example 2 was almost equal to crash strength of the granules according to Example 1.

It is understood from the results of Table 1 and Table 2 that milling of the catalyst powder of homogeneous nanometer size becomes possible in a short time. Furthermore, it is possible to obtain compact, spherical granules, as shown in FIGS. 1 and 2, by spray drying the milled catalyst powder. Furthermore, as is clear from the results of Table 3, it is possible to obtain a higher crash strength by granules of Example 1 obtained by aging and then spray drying a catalyst powder-containing slurry milled by the bead mill, as compared with a catalyst powder of Comparative Example 1 of a nano-size (crystal size: 80 nm) obtained by simply spray drying a slurry. Furthermore, it was shown that, since the granules of Example 1 have an increased crystal surface area resulting from the milling of the contained catalyst powder, the efficiency of the contact with the reaction gas increases, and they can act as efficient catalyst granules even in a reaction under a high flow rate condition, such as flow bed process. It was also confirmed that the above crash strength can be obtained by milling the metallosilicate raw material by a bead mill in a manner that the particle size of the metallosilicate becomes 1.0 μm or less, particularly 0.5 μm or less, at a cumulative frequency of 50%.

EXAMPLE 3

As a catalyst powder according to Example 3, there was used a type of metallosilicate, ZSM-5, having an average particle size of 42 μm and a crystalline size of 5 μm. The catalyst powder raw material was of ammonia-type and converted to proton-type by conducting a baking treatment at a predetermined temperature. Metal was not supported on ZSM-5 used in the present example.

Firstly, the milling method of the catalyst powder by a bead mill is explained. 20 kg of purified water was weighed relative to 5 kg of the catalyst powder, and the total amount of the purified water was put into a stirring container. While rotating a blade of a stirrer, the total amount of the catalyst powder was added at 400 g/minute. After that, a slurry-circulating pump was energized, and it was started to circulate and mill the slurry. In 1 hr after the start of the milling, the milling was conducted until a crystalline size of 0.2 μm. After stopping the circulating pump, the slurry in the system was taken. The recovered slurry was 18.9 kg relative to 25 kg of the weight of the slurry introduced.

Then, the granulation method of the catalyst powder by a spray dryer is explained. The slurry formerly prepared was subjected to an aging for 5 days. In the aging, the slurry was allowed to stand still in the atmosphere of air of normal temperature and normal pressure. Then, the stirring was conducted in a stirring container. After setting at an inlet temperature of 230-240° C. and an outlet temperature of 90° C., drying and granulation were started by a spray dryer (Type DL-41 made by YAMATO SCIENTIFIC CO., LTD.) under conditions of a dry air wind rate of 0.8 $m^3$/min, a nozzle spray air pressure of 0.1 MPa, and a slurry feed rate of 20 g/min. The obtained granules were dried in the air at 120° C. for 20 hr. Then, a baking was conducted for 5 hours under 550° C.

Regarding strength of the granules obtained, crash strength of 15 granules was measured by a measurement method in accordance with JIS Z8841. The measurement results are shown in Table 4. The average crash strength of the granules was not higher than 60.8 gf/$mm^2$.

Flow property of the granules was based on the bulk density measurement method according to JIS Z2504 and JIS R6126 (to obtain flow property index from the way of decrease of bulk by conducting tapping). The measurement was conducted according to Kawakami's way tap density measurement method. The measurement result is shown in Table 5. A smaller value in Kawakami's way flow property index means being better in flow property. Flow property index of the granules was 0.38.

EXAMPLE 4

As to the catalyst powder according to Example 4, molybdenum as a metal component is supported on the metallosilicate. Furthermore, the catalyst production method of the present example is the same as the catalyst production method according to Example 3, except in having a procedure of supporting a metal component by impregnation on the catalyst powder milled by a bead mill.

Firstly, there is explained a method of impregnation and supporting of a metal to be supported, after milling of the catalyst powder by a bead mill. 2kg of the slurry prepared under the same conditions as those of Example 3 was aged for 5 days, followed by stirring in a stirring container. Then, to this slurry, there was added an aqueous solution prepared by dissolving 42 g of ammonium heptamolybdate in 200 g of water, and then stirring was conducted for 3 hr.

Then, the granulation method of the catalyst powder by a spray dryer is explained. After setting the slurry prepared as above at an inlet temperature of 230-240° C. and an outlet temperature of 90° C., drying and granulation were started by a spray dryer (Type DL-41 made by YAMATO SCIENTIFIC CO., LTD.) under conditions of a dry air wind rate of 0.8 $m^3$/min, a nozzle spray air pressure of 0.1 MPa, and a slurry feed rate of 20 g/min. The obtained granules were dried in the air at 120° C. for 20 hr. Then, a baking was conducted for 5 hours under 550° C.

Figure 5:
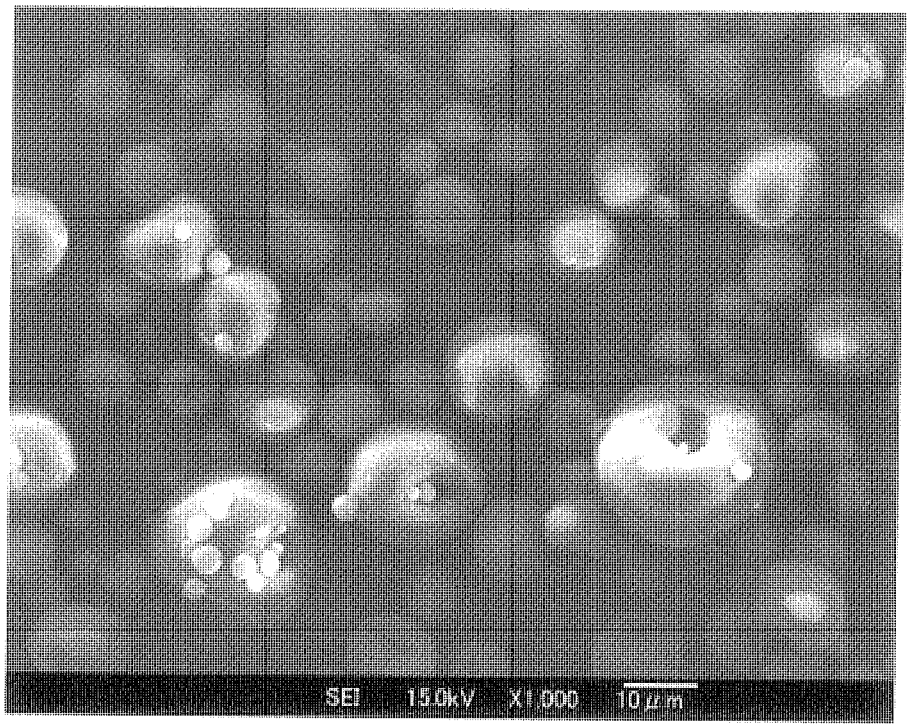
FIG. 5 is an SEM photograph (accelerating voltage: 15.0 kV; magnification: 1,000) of granules of Example 4.
Figure 6:
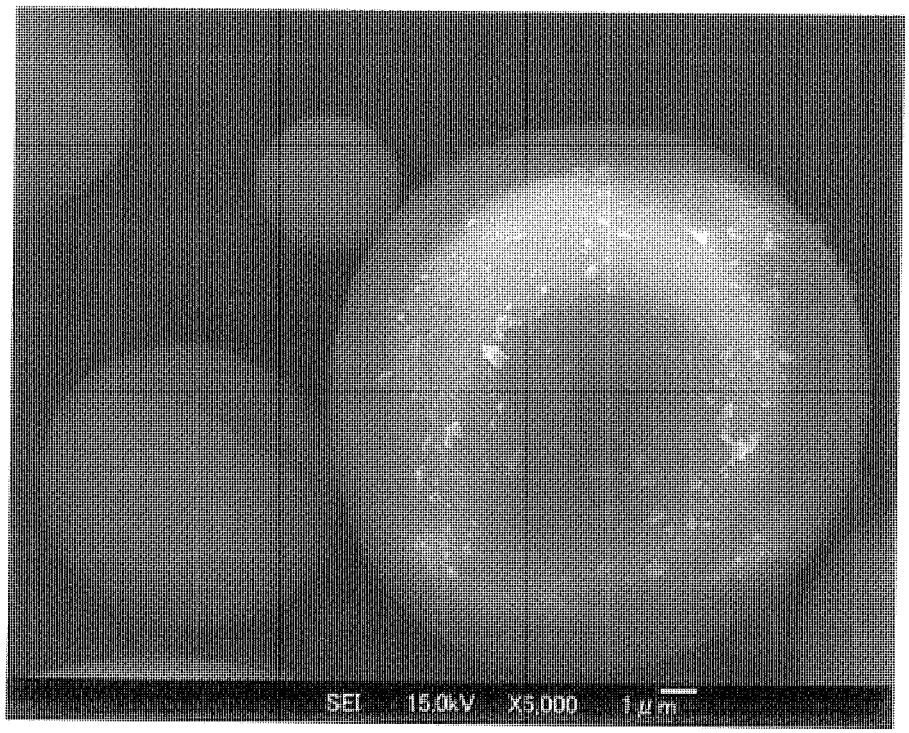
FIG. 6 is an SEM photograph (accelerating voltage: 15.0 kV; magnification: 5,000) of granules of Example 4.
Figure 7:
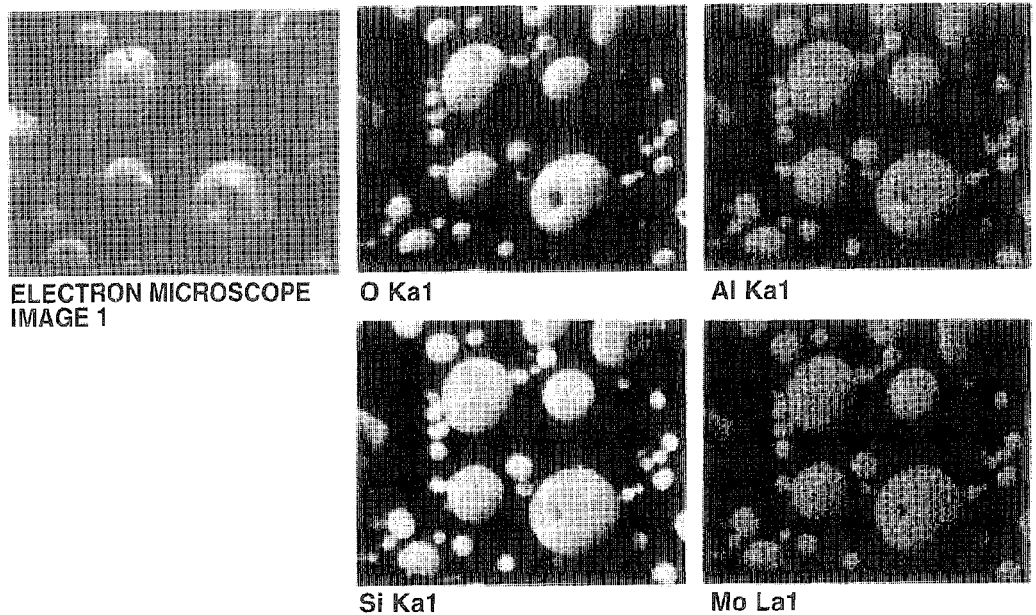
FIG. 7 is an SEM photograph (magnification: 1,000) showing distributions of elements (O, Al, Si, and Mo) on the surface of granules of Example 4.

The result (the average of ten points) of crash strength of the granules is shown in Table 4, and the result of flow property index is shown in Table 5. The measurements of crash strength and flow property index were conducted in the same methods as those of Example 3. SEM photographs of the granules after the baking are shown in FIG. 5 (magnification: 1,000) and FIG. 6 (magnification: 5,000). Furthermore, SEM photographs showing the distribution of elements (O, Al, Si, and Mo) on the surface of the granules are shown in FIG. 7 (magnification: 1,000) and FIG. 8 (magnification: 10,000).

EXAMPLE 5

The catalyst production method of the present example is the same as the catalyst production method according to Example 4, except in that it has a procedure of further adding a PVA aqueous solution to the slurry into which an ammonium heptamolybdate aqueous solution was introduced.

That is, 2 kg of the slurry prepared under the same conditions as those of Example 3 was aged for 5 days, followed by stirring in a stirring container. Then, into this slurry, there was introduced an aqueous solution prepared by dissolving 42 g of ammonium heptamolybdate in 200 g of water. Furthermore, 8 g of 10% PVA aqueous solution was added, followed by stirring for 3 hours. The subsequent granulation method is the same as the catalyst granulation procedure according to Example 4.

Figure 9:
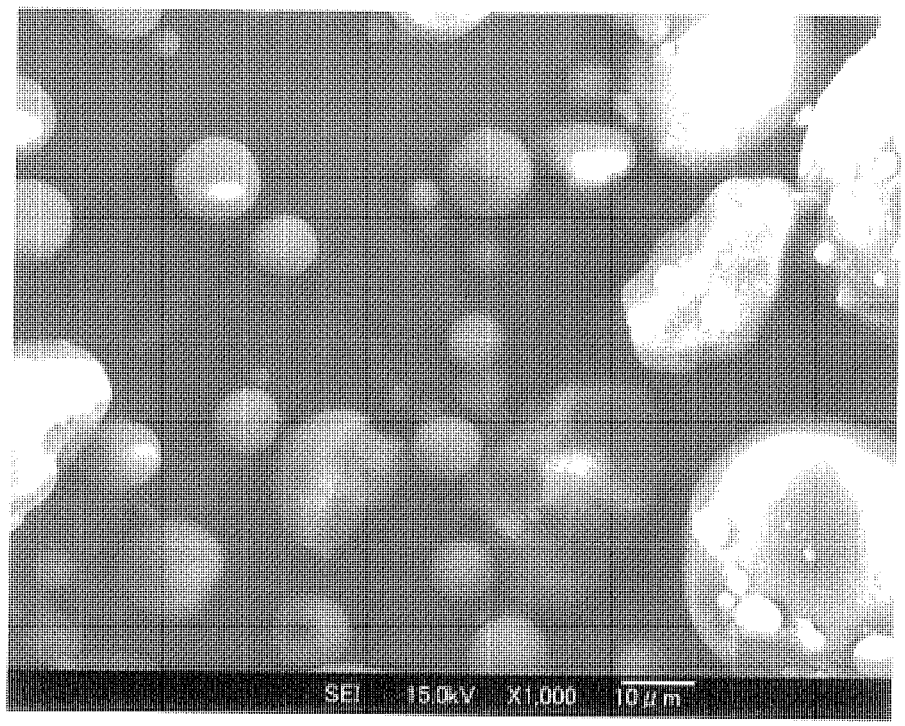
FIG. 9 is an SEM photograph (accelerating voltage: 15.0 kV; magnification: 1,000) of granules of Example 5.
Figure 10:
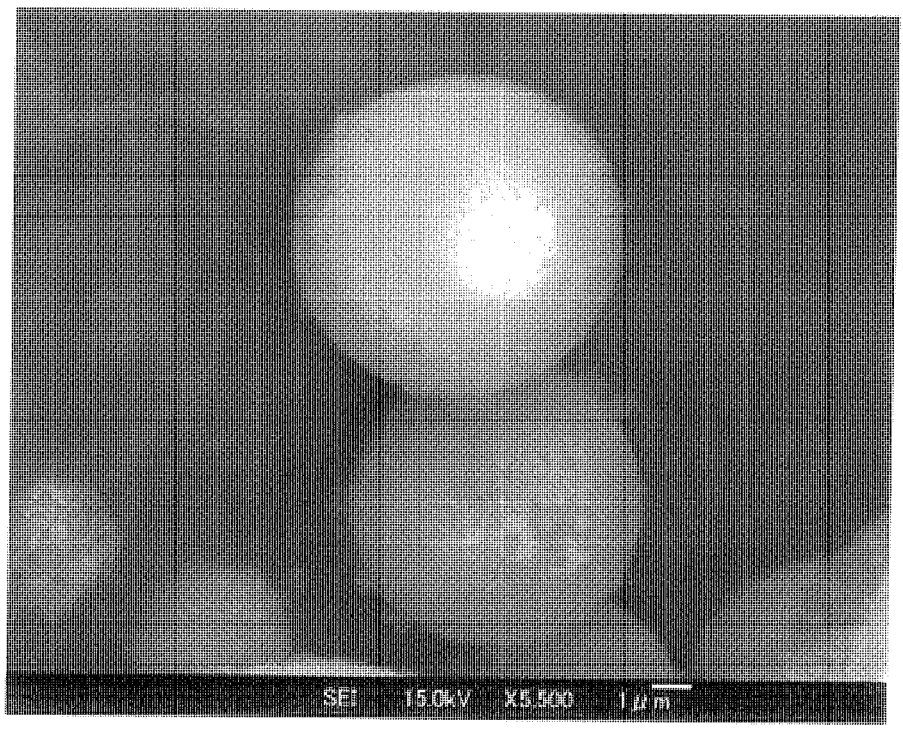
FIG. 10 is an SEM photograph (accelerating voltage: 15.0 kV; magnification: 5,500) of granules of Example 5.
Figure 11:
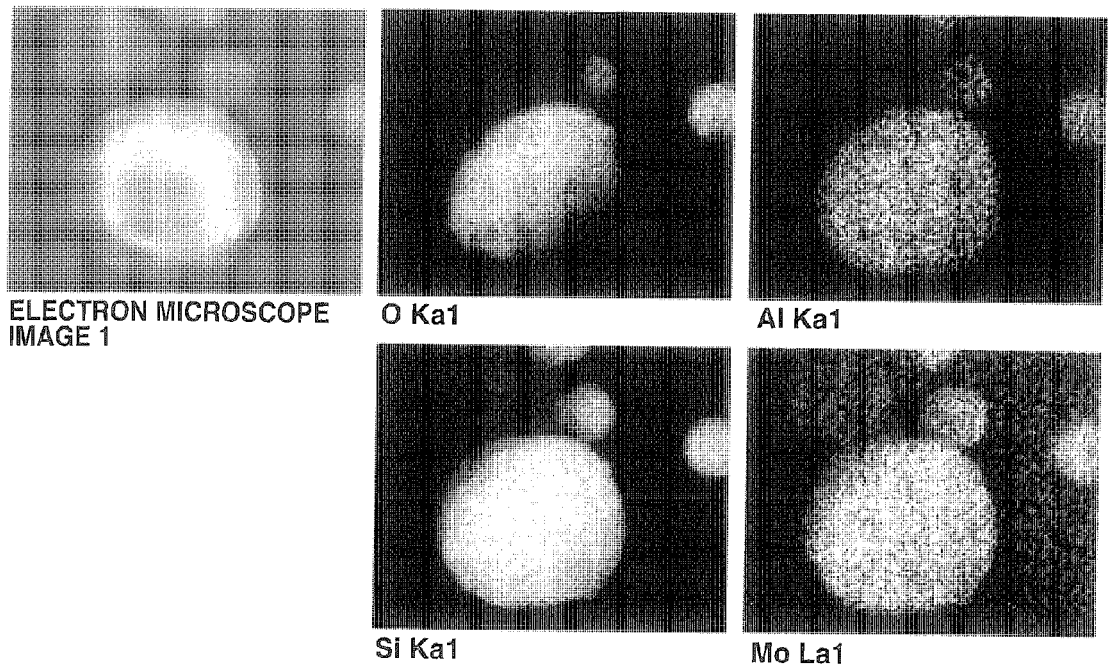
FIG. 11 is an SEM photograph (magnification: 10,000) showing distributions of elements (O, Al, Si, and Mo) on the surface of granules of Example 5.

The result (the average of ten points) of crash strength of the granules is shown in Table 4, and the result of flow property index is shown in Table 5. The measurements of crash strength and flow property index were conducted in the same methods as those of Example 3. SEM photographs of the granules after the baking are shown in FIG. 9 (magnification: 1,000) and FIG. 10 (magnification: 5,500). Furthermore, SEM photographs (magnification: 10,000) showing distribution of elements (O, Al, Si, and Mo) on the surface of the granules are shown in FIG. 11.

It is understood from the results of Table 4 that the granules of Example 4 obtained by supporting molybdenum by impregnation on the slurry, spray drying, and baking have a higher crash strength, as compared with spray drying and baking of a nano-size raw material slurry such as that of Example 3. Furthermore, it is understood that the granules of Example 5 obtained by adding PVA, spray drying and baking have a higher crash strength.

According to the results of Table 5, it is understood that the catalysts of Examples 4 and 5 are granules superior in flow property, since their flow property indexes are each lower than that of the catalyst of Example 3.

As shown in FIG. 5 to FIG. 8, compact, spherical granules are obtained as granules of Example 4. Furthermore, as shown in FIG. 9 to FIG. 11, it was confirmed that granules with little defect (depression) are obtained according to the catalyst production method of Example 5, to which PVA was added. The catalyst powder in the granules has an increased area of the crystal surface by the milling. Therefore, the efficiency of the contact with the reaction gas increases, and they can act as efficient catalyst granules even in a reaction under a high flow rate condition, such as flow bed process.

Figure 8:
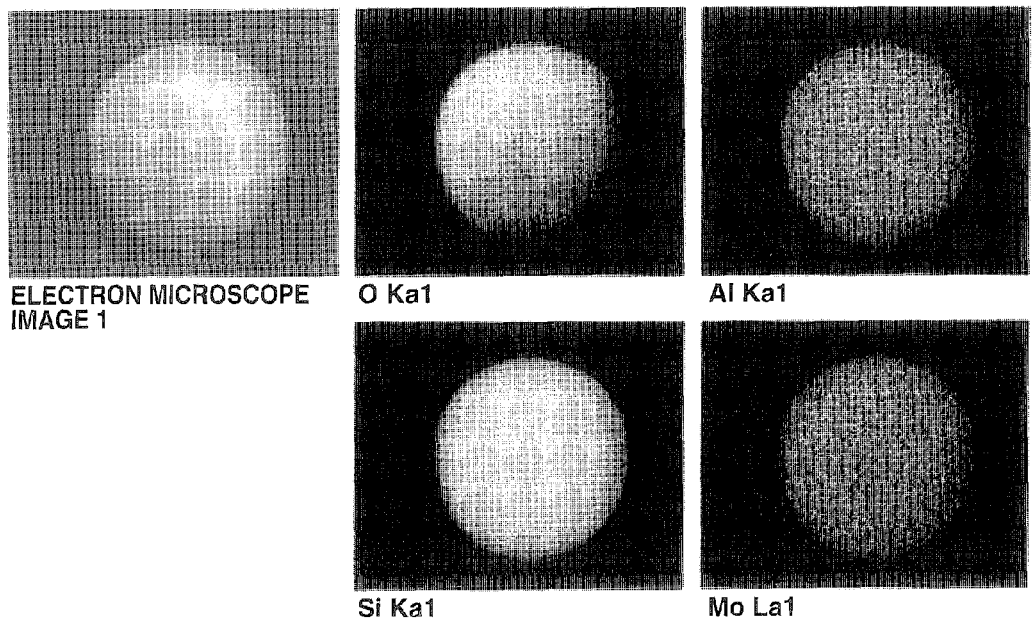
FIG. 8 is an SEM photograph (magnification: 10,000) showing distributions of elements (O, Al, Si, and Mo) on the surface of granules of Example 4.

Furthermore, in the element distribution photographs of FIG. 7, FIG. 8 and FIG. 11, the photographs of "O Kα1" show oxygen distribution. The photographs of "Al Kα1" show aluminum distribution. The photographs of "Si Kα1" show silicon distribution. The photographs of "Mo Lα1" show molybdenum distribution. White parts of the photographs show the distribution of the elements. According to the above photographs, it is possible to confirm that the metal element components (Al and Mo) are supported on the surface of the granules under a uniformly distributed condition. It is possible to confirm that Si is densely distributed over the whole surface, since main components of zeolite used in examples are $AlO_3$ and $SiO_2$, and since the $SiO_2/Al_2O_3$ ratio of the main raw material is 40.

As is clear from the results of the above examples, according to the catalyst production process of the present invention, the effective area of the crystal surface part of the catalyst increases by milling of the nano-size catalyst powder by the bead mill. It becomes easily possible to produce spherical granules, which has been difficult by rolling granulation method. Furthermore, it is possible to omit or greatly reduce the inorganic caking agent. Then, it becomes easy to have a uniform metal supporting on a catalyst powder contained in granules by impregnating the catalyst powder with the metal component by adding the metal component, which is exemplified by molybdenum, to a slurry containing the milled catalyst powder. Furthermore, it is possible to make flow property of the granules better. Furthermore, crash strength of the granules becomes high. In particular, it is possible to further increase crash strength by adding PVA.

TABLE 1

Particle Size Distribution of Catalyst Powder (Example 1) Milled by Bead Mill

| Cumulative (%) | Particle Size (μm) | | | | |
|---|---|---|---|---|---|
| | 0 min | 15 min | 30 min | 45 min | 60 min |
| 10 | 7.137 | 0.478 | 0.351 | 0.214 | 0.184 |
| 20 | 9.594 | 0.560 | 0.409 | 0.269 | 0.231 |
| 30 | 11.43 | 0.633 | 0.456 | 0.314 | 0.270 |
| 40 | 13.04 | 0.716 | 0.500 | 0.357 | 0.307 |
| 50 | 14.63 | 0.816 | 0.546 | 0.398 | 0.346 |
| 60 | 16.33 | 0.950 | 0.598 | 0.442 | 0.387 |
| 70 | 18.33 | 1.139 | 0.662 | 0.495 | 0.436 |
| 80 | 21.01 | 1.424 | 0.755 | 0.565 | 0.502 |
| 90 | 25.68 | 1.946 | 0.926 | 0.687 | 0.617 |
| 95 | 30.75 | 2.548 | 1.123 | 0.825 | 0.748 |

TABLE 2

Particle Size Distribution of Catalyst Powder (Example 2) Milled by Bead Mill

| Cumulative (%) | Particle Size (μm) | | | | |
|---|---|---|---|---|---|
| | 0 min | 15 min | 30 min | 45 min | 60 min |
| 10 | 3.010 | 0.478 | 0.338 | 0.214 | 0.180 |
| 20 | 4.147 | 0.554 | 0.396 | 0.267 | 0.224 |
| 30 | 5.264 | 0.624 | 0.443 | 0.313 | 0.261 |
| 40 | 6.503 | 0.702 | 0.488 | 0.357 | 0.298 |
| 50 | 8.062 | 0.799 | 0.535 | 0.399 | 0.336 |
| 60 | 10.35 | 0.935 | 0.588 | 0.455 | 0.378 |
| 70 | 14.09 | 1.143 | 0.655 | 0.500 | 0.427 |
| 80 | 19.94 | 1.472 | 0.753 | 0.573 | 0.496 |
| 90 | 29.51 | 2.095 | 0.943 | 0.707 | 0.618 |
| 95 | 39.31 | 2.826 | 1.175 | 0.861 | 0.758 |

TABLE 3

| | Crash Strength (gf/mm$^2$) |
|---|---|
| Comparative Example 1 | Less than 0.06 |
| Example 1 | 60.8 |

TABLE 4

Crash Strength of Granules (gf/mm$^2$)

| | Granule Size | |
|---|---|---|
| | 40-125 μm | 125-250 μm |
| Example 3 | | 66.2 |
| Example 4 | 607.7 | 349.2 |
| Example 5 | 848.8 | |

TABLE 5

Flow Property Index of Granules

| | Granule Size 40-125 μm |
|---|---|
| Example 3 | 0.38 |
| Example 4 | 0.28 |
| Example 5 | 0.29 |

The invention claimed is:

1. A process for producing a catalyst that is used for producing an aromatic compound and hydrogen from a lower hydrocarbon, comprising the steps of:
   (a) milling a zeolite material-containing raw material by a wet milling process to obtain a slurry containing a catalyst powder including particles such that half the particles have a size of 1.0 μm or less;
   (b) adding a metal component to the slurry obtained by step (a), the metal component being at least one selected from the group consisting of rhenium, vanadium, molybdenum, tunosten, chromium and their compounds; and
   (c) drying the slurry obtained by step (b) by a spray drying method to obtain granules of a catalyst, the metal component being supported on the granules.

2. A process according to claim 1, wherein the milling is conducted by a bead mill.

3. A process according to claim 1, wherein the slurry is subjected to an aging between the steps (a) and (b).

4. A process according to claim 3, wherein the aging is conducted by allowing the slurry to stand still under an atmosphere of an air of normal temperature and normal pressure.

5. A process according to claim 1, wherein the zeolite material-containing raw material contains a zeolite material having micropores of a size that is substantially 4.5 to 6.5 angstroms.

6. A process according to claim 1, wherein an amount of the molybdenum supported is 2-12 weight % relative to the total amount of the catalyst powder.

7. A process according to claim 1, wherein polyvinyl alcohol is added to the slurry.

8. A process according to claim 1, wherein molybdenum as the metal component is supported on ZSM-5 as the zeolite material.

* * * * *